US00PP31084P2

(12) United States Plant Patent
Wood

(10) Patent No.: US PP31,084 P2
(45) Date of Patent: Nov. 19, 2019

(54) ***LYCIUM* PLANT NAMED 'SMNLBBB'**

(50) Latin Name: *Lycium barbarum*
Varietal Denomination: SMNLBBB

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/350,436

(22) Filed: Nov. 15, 2018

(51) Int. Cl.
*A01H 5/02* (2018.01)
*A01H 6/82* (2018.01)
*A01H 5/08* (2018.01)

(52) U.S. Cl.
USPC ..... Plt./226
CPC ..... *A01H 6/82* (2018.05); *A01H 5/02* (2013.01); *A01H 5/08* (2013.01)

(58) Field of Classification Search
USPC ..... Plt./226, 156
CPC ..... A01H 6/82; A01H 5/02; A01H 5/08
See application file for complete search history.

*Primary Examiner* — Kent L Bell
(74) *Attorney, Agent, or Firm* — C. A. Whealy

(57) ABSTRACT

A new and distinct *Lycium* plant named 'SMNLBBB', characterized by its upright to outwardly arching plant habit; freely branching habit; dense and bushy growth habit; yellow green-colored leaves; purple violet-colored flowers; large, numerous and attractive orange red-colored fruits; and good garden performance.

3 Drawing Sheets

Botanical designation: *Lycium barbarum.*
Cultivar denomination: 'SMNLBBB'.

BACKGROUND OF THE INVENTION

The present Invention relates to a new and distinct *Lycium* plant, botanically known as *Lycium barbarum* and hereinafter referred to by the name 'SMNLBBB'.

The new *Lycium* plant is a product of a planned breeding program conducted by the Inventor in Grand Haven, Mich. The objective of the breeding program was to develop new large *Lycium* plants that produce large, numerous and attractive fruits.

The new *Lycium* plant originated from an open-pollination during the summer of 2012 of *Lycium barbarum* 'SMNDBL', not patented, as the female, or seed, parent with an unknown selection of *Lycium barbarum*, as the male, or pollen, parent. The new *Lycium* plant was discovered and selected by the Inventor in 2015 as a single plant within the progeny of the stated open-pollination in a controlled environment in Grand Haven, Mich.

Asexual reproduction of the new *Lycium* plant by softwood cuttings in Grand Haven, Mich. since 2015 has shown that the unique features of the new *Lycium* plant are stable and reproduced true to type in successive generations of asexual reproduction.

SUMMARY OF THE INVENTION

Plants of the new *Lycium* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'SMNLBBB'. These characteristics in combination distinguish 'SMNLBBB' as a new and distinct *Lycium* plant:

1. Upright to outwardly arching plant habit.
2. Freely branching habit; dense and bushy growth habit.
3. Yellow green-colored leaves.
4. Purple violet-colored flowers.
5. Large, numerous and attractive orange red-colored fruits.
6. Good garden performance.

Plants of the new *Lycium* differ primarily from plants of the female parent, 'SMNDBL', in fruit production as plants of the new *Lycium* produce more fruits per plant than plants of 'SMNDBL'. In addition, fruits of plants of the new *Lycium* are larger than fruits of plants of 'SMNDBL'.

Plants of the new *Lycium* can be compared to the plants of *Lycium barbarum* 'SMNDSL' not patented. In side-by-side comparisons, plants of the new *Lycium* differ from plants of 'SMNDSL' in the following characteristics:

1. Plants of the new *Lycium* have lighter purple violet-colored flowers than plants of 'SMNDSL'.
2. Plants of the new *Lycium* produce more fruits per plant than plants of 'SMNDSL'.
3. Fruits of plants of the new *Lycium* are larger than fruits of plants of 'SMNDSL'.

BRIEF DESCRIPTION OF THE PHOTOGRAPHS

The accompanying colored photographs illustrate the overall appearance of the new *Lycium* plant. The photographs show the colors as true as it is reasonably possible to obtain in colored reproductions of this type. Colors in the photographs may differ slightly from the color values cited in the detailed botanical description which accurately describe the colors of the new *Lycium* plant.

The photograph on the first sheet is a side perspective view of a typical plant of 'SMNLBBB' grown in a container.

The photograph on the second sheet is a close-up view of a typical flower and leaves of 'SMNLBBB'.

The photograph on the third sheet is a close-up view of lateral branch with typical fruits of 'SMNLBBB'.

DETAILED BOTANICAL DESCRIPTION

The aforementioned photographs and following observations and measurements describe plants grown during the summer in three-gallon containers in a polyethylene-covered greenhouse in Grand Haven, Mich. and under cultural practices typical of commercial *Lycium* production. During the production of the plants, day temperatures ranged from 18° C. to 27° C. and night temperatures ranged from 5° C. to 10° C. Plants were three years old when the photographs and detailed description were taken. In the following description, color references are made to The Royal Horticultural Society Colour Chart, 2015 Edition, except where general terms of ordinary dictionary significance are used.

Botanical classification: *Lycium barbarum* 'SMNLBBB'.

Parentage:

*Female, or seed, parent.*—*Lycium barbarum* 'SMNDBL', not patented.

*Male, or pollen, parent.*—Unknown selection of *Lycium barbarum*, not patented.

Propagation:

*Type.*—By softwood cuttings.

*Time to initiate roots, winter.*—About four weeks at temperatures about 18° C. to 27° C.

*Time to produce a rooted young plant, summer.*—About three months at temperatures about 18° C. to 27° C.

*Root description.*—Medium in thickness, fibrous; typically white to brown in color, actual color of the roots is dependent on substrate composition, water quality, fertilizer, substrate temperature and physiological age of roots.

*Rooting habit.*—Freely branching; medium density.

Plant description:

*Plant and growth habit.*—Perennial evergreen shrub; upright and outwardly arching plant habit; moderately vigorous growth habit.

*Branching habit.*—Freely branching habit; dense and bushy growth habit with about 16 lateral branches developing per plant.

*Plant height.*—About 95 cm.

*Plant diameter, area of spread.*—About 137 cm.

*Lateral branch description.*—Length: About 94 cm. Diameter: About 8 mm. Internode length: About 1.5 cm. Strength: Strong. Aspect: About 15° to 35° from vertical. Texture: Smooth, glabrous; becoming woody with development. Color, developing: Close to 195A. Color, developed: Close to 197B.

*Leaf description.*—Arrangement: Opposite, simple. Length: About 3.25 cm. Width: About 1.25 cm. Shape: Narrowly elliptic. Apex: Acute. Base: Attenuate. Margin: Entire. Venation pattern: Pinnate. Texture, upper and lower surfaces: Smooth, glabrous. Color: Developing leaves, upper surface: Close to 144B. Developing leaves, lower surface: Close to 144C. Fully expanded leaves, upper surface: Close to 151A; venation, close to 182B. Fully expanded leaves, lower surface: Close to N144D; venation, close to 196A. Petioles: Length: About 1 cm. Diameter: About 2 mm. Texture, upper and lower surfaces: Smooth, glabrous. Color, upper surface: Close to 178B. Color, lower surface: Close to 194D. Thorns: Length: About 4 mm. Diameter: Less than 1 mm. Texture: Smooth, glabrous. Color: Close to 195A.

Flower description:

*Flower appearance and arrangement.*—Single axillary star-shaped flowers; flowers face mostly outwardly to downward; freely flowering habit with about 100 flowers developing per plant during the flowering season.

*Natural flowering season.*—Plants flower during the summer in Michigan; flowers persistent.

*Fragrance.*—None detected.

*Flower diameter.*—About 1.5 cm.

*Flower length (height).*—About 1 cm.

*Flower buds.*—Length: About 1 cm. Diameter: About 5 mm. Shape: Spherical. Color: Close to 85A and 123A.

*Petals.*—Quantity and arrangement: About five in a single whorl. Length: About 5 mm. Width: About 4.5 mm. Shape: Obovate. Apex: Obtuse. Base: Truncate. Margin: Sinuate. Texture, upper and lower surfaces: Smooth, glabrous. Color: When opening and fully opened, upper surface: Close to N80B; center, close to N92B; color becoming closer to 161C with development. When opening and fully opening, lower surface: Close to N80D; color becoming closer to 161D with development.

*Sepals.*—Quantity and arrangement: About three in a single whorl. Length: About 2 mm. Diameter: About 2 mm. Shape: Deltoid. Apex: Acute. Base: Fused. Margin: Entire. Texture, upper and lower surfaces: Smooth, glabrous. Color, upper and lower surfaces: Close to N82D.

*Peduncles.*—Length: About 1.25 cm. Diameter: About 1 mm. Aspect: About 90° to 135° from the stem axis. Strength: Moderately strong; flexible. Texture: Smooth, glabrous. Color: Close to N79D.

*Reproductive organs.*—Androecium: Quantity per flower: About five. Filament length: About 5 mm. Filament color: Close to 157B. Anther length: About 1.75 mm. Anther shape: Club-shaped. Anther color: Close to 158A. Pollen amount: Moderate. Pollen color: Close to 158A. Gynoecium: Quantity per flower: One. Pistil length: About 1.2 cm. Style length: About 1.2 cm. Style color: Close to 157B. Stigma shape: Globular. Stigma color: Close to 157B. Ovary color: Close to 157B.

*Fruits.*—Quantity per plant: About 100 during the flowering season. Length: About 1.75 cm. Diameter: About 1 cm. Shape: Spherical. Texture: Smooth, slightly undulate. Color: Close to N30A.

Garden performance: Plants of the new *Lycium* have been observed to have good garden performance and to be tolerant to rain, wind and temperatures ranging from about −32° C. to about 36° C.

Pathogen & pest resistance: Plants have not been observed to be resistant to pathogens and pests common to *Lycium* plants.

It is claimed:

1. A new and distinct *Lycium* plant named 'SMNLBBB' as illustrated and described.

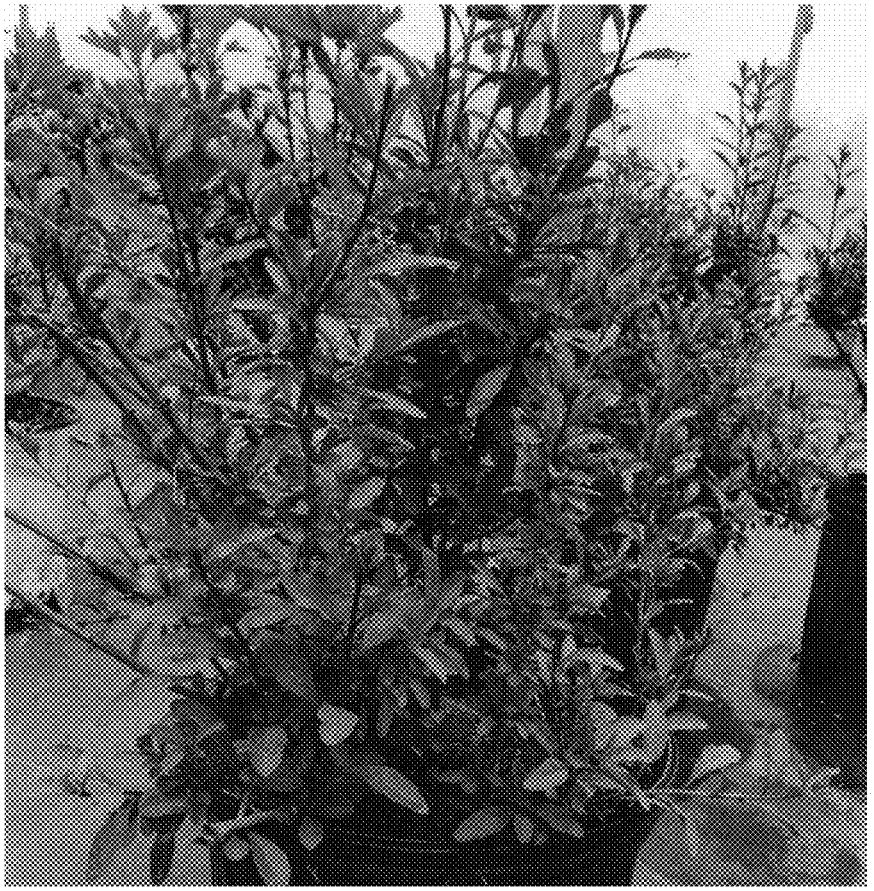

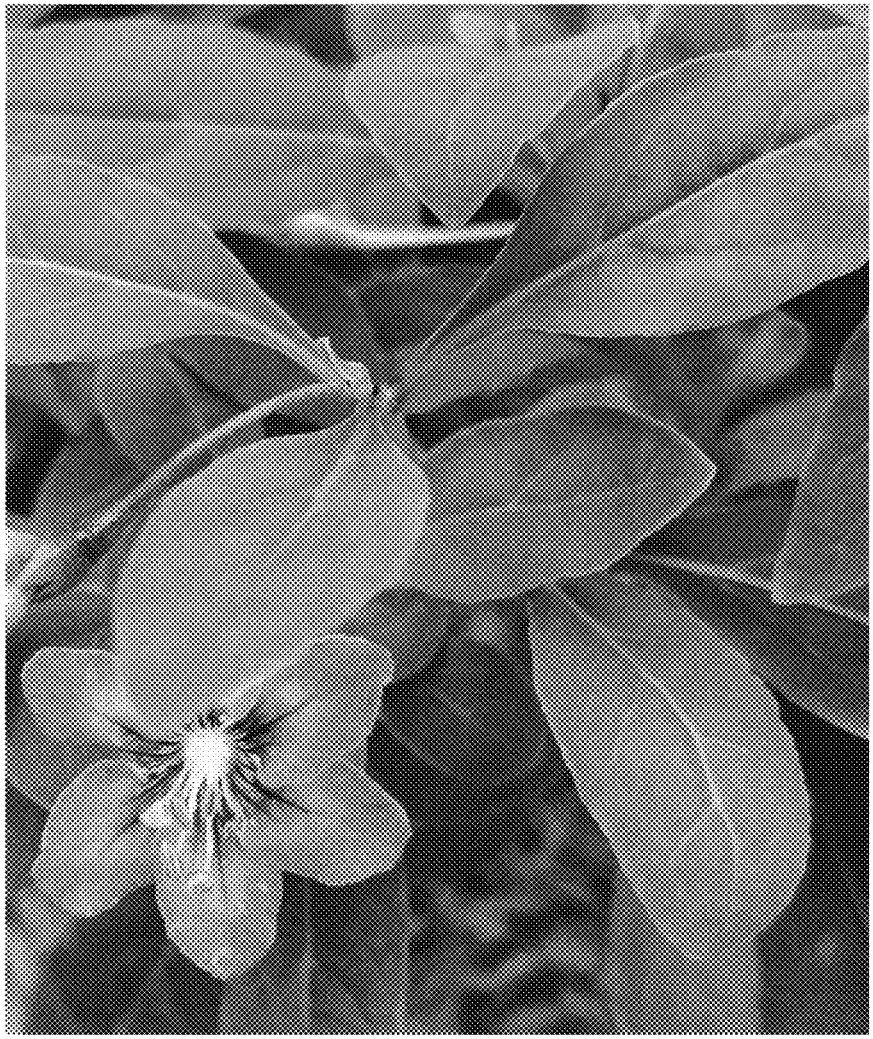

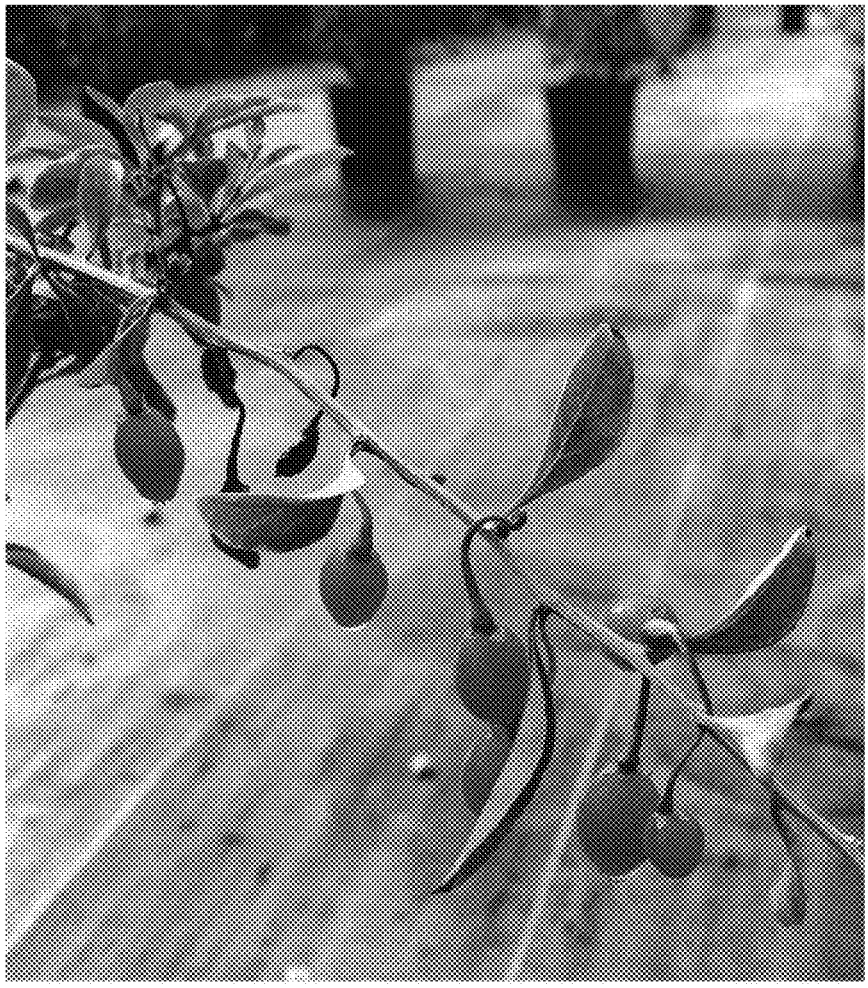

* * * * *